(12) United States Patent
Rogers et al.

(10) Patent No.: US 9,675,520 B2
(45) Date of Patent: Jun. 13, 2017

(54) ASEPTIC SAMPLING SYSTEM

(75) Inventors: Samson Salman Rogers, Beds (GB); David Micah Katz, Surrey (GB); Neil Pollock, Melbourn (GB)

(73) Assignee: Pall Corporation, Port Washington, NY (US)

( * ) Notice: Subject to any disclaimer, the term of this patent is extended or adjusted under 35 U.S.C. 154(b) by 899 days.

(21) Appl. No.: 13/971,995

(22) PCT Filed: Feb. 22, 2012

(86) PCT No.: PCT/GB2012/050396
§ 371 (c)(1),
(2), (4) Date: Aug. 6, 2014

(87) PCT Pub. No.: WO2012/114105
PCT Pub. Date: Aug. 30, 2012

(65) Prior Publication Data
US 2014/0345748 A1 Nov. 27, 2014

(30) Foreign Application Priority Data
Feb. 22, 2011 (GB) .................................. 1103068.1

(51) Int. Cl.
*A61J 1/20* (2006.01)
*A61M 39/18* (2006.01)
(Continued)

(52) U.S. Cl.
CPC ............... *A61J 1/2096* (2013.01); *A61J 1/12* (2013.01); *A61J 1/1475* (2013.01); *A61M 39/18* (2013.01);
(Continued)

(58) Field of Classification Search
CPC .... A61J 1/2096; A61M 39/18; Y10S 604/905
(Continued)

(56) References Cited

U.S. PATENT DOCUMENTS 4,019,512 A * 4/1977 Tenczar ................ A61M 39/14
222/80
4,056,981 A 11/1977 Kalka et al.
(Continued)

FOREIGN PATENT DOCUMENTS

CN 1829631 A 9/2006
JP 55-501107 A 12/1980
(Continued)

OTHER PUBLICATIONS

Notice of Reasons for Rejection, Japanese Application No. P2013-554941, dated Aug. 12, 2014.
(Continued)

*Primary Examiner* — Timothy L Maust
*Assistant Examiner* — Timothy P Kelly
(74) *Attorney, Agent, or Firm* — Jeremy Jay

(57) ABSTRACT

An aseptic sampling system comprises sampler and interface assemblies. Each assembly comprises a housing defining separate sterile enclosures. An air lock provides aseptic joining of the enclosures within the sampler and interface assemblies, and a re-sealable liquid connection mechanism operates within the lock. The sampler and interface assemblies, when connected, form an outer protective surface comprising the housings of the sampler and interface assemblies, the protective surface providing a sterile internal enclosure and air lock and an air-tight barrier between outer non-sterile, and inner sterile, atmospheres. The connection mechanism, contained within the sterile enclosure, contains at least one liquid connector from each of the sampler and interface assemblies, configured such that at least one of the connectors moves across the enclosure and lock to connect with the other connector in the connection mechanism, without contacting internal surfaces within the lock, and the connectors can be re-sealed, disconnected and separated.

8 Claims, 14 Drawing Sheets

(51) Int. Cl.
*B01L 1/02* (2006.01)
*G01N 1/10* (2006.01)
*B01L 3/00* (2006.01)
*A61J 1/12* (2006.01)
*A61J 1/14* (2006.01)
*G01N 1/20* (2006.01)

(52) U.S. Cl.
CPC ............... *B01L 1/02* (2013.01); *B01L 3/563* (2013.01); *G01N 1/10* (2013.01); *A61J 1/1481* (2015.05); *B01L 2300/0672* (2013.01); *B01L 2400/0478* (2013.01); *B01L 2400/0644* (2013.01); *G01N 2001/1037* (2013.01); *G01N 2001/205* (2013.01)

(58) Field of Classification Search
USPC .................................................. 141/329, 383
See application file for complete search history.

(56) References Cited

U.S. PATENT DOCUMENTS

| | | | |
|---|---|---|---|
| 4,306,705 A * | 12/1981 | Svensson | A61B 5/20 251/148 |
| 4,564,054 A | 1/1986 | Gustavsson | |
| 5,620,114 A | 4/1997 | Chalfa | |
| 6,155,027 A | 12/2000 | Brooks | |
| 7,137,974 B2 * | 11/2006 | Almasian | A61M 39/14 137/614 |
| 7,523,918 B2 | 4/2009 | Matkovich et al. | |
| 2005/0090797 A1 | 4/2005 | Almasian et al. | |
| 2007/0191167 A1 | 8/2007 | Koch et al. | |
| 2007/0277478 A1 | 12/2007 | Koch et al. | |
| 2012/0085182 A1 | 4/2012 | Untch | |

FOREIGN PATENT DOCUMENTS

| | | |
|---|---|---|
| JP | 2005-532889 A | 11/2005 |
| JP | 2007-500660 A | 1/2007 |
| JP | 4-83255 B2 | 4/2008 |
| WO | WO 80/01507 A1 | 7/1980 |
| WO | WO 2012/114105 A1 | 8/1996 |
| WO | WO 96/29587 A1 | 9/1996 |
| WO | WO 2010/121690 A1 | 10/2010 |

OTHER PUBLICATIONS

International Preliminary Report on Patentability, International Application No. PCT/GB2012/050396, dated Aug. 27, 2013.
International Search Report, Appln. No. PCT/GB2012/050396, mailed on Jun. 5, 2012.
Office Action, Chinese Application No. 201280009898.8 dated Sep. 15, 2014.

* cited by examiner

Figure 1
Figure 1a
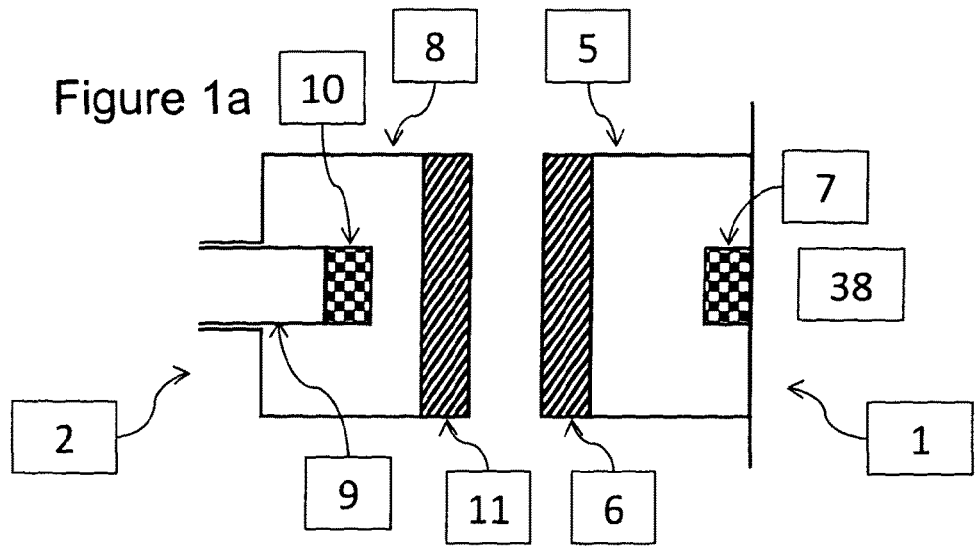
Figure 1bi
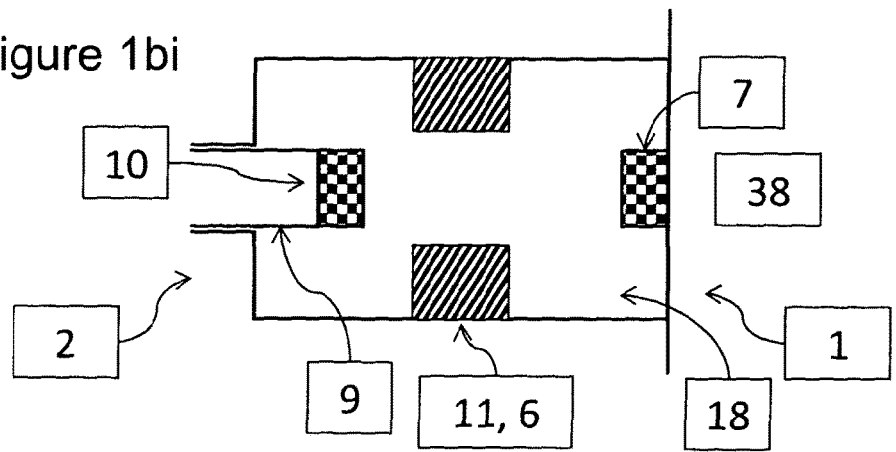
Figure 1bii
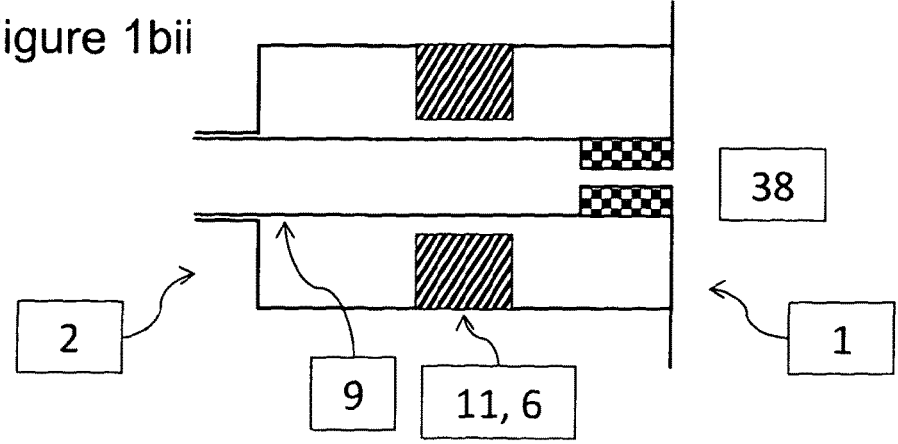

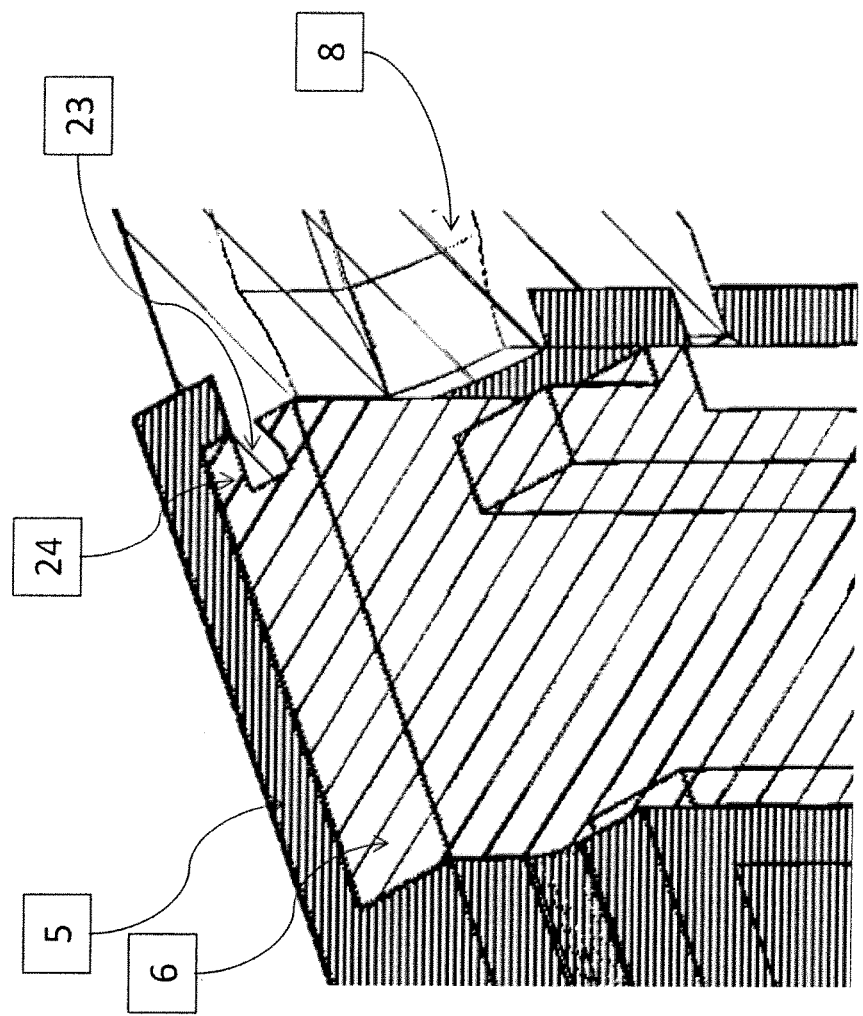

ASEPTIC SAMPLING SYSTEM

The present invention relates to an aseptic sampling system. In industries such as bioprocessing and medical devices, there is an identified need for the aseptic and ultra clean removal and injection of multiple samples from a reservoir. The sample and reservoir must not be contaminated by infectious agents that may be present in the atmosphere or on the surfaces outside the vessel. The present invention seeks to address the need for a sterile, ultra clean, fluidic connection to be made and broken, time after time, without contaminating any of the sample, any mechanism in the sampler that is in contact with the sample or reservoir, or the liquid in the reservoir itself. The name for this process is 'aseptic sampling'.

In the medical industry, for example in intravenous therapy, clean sampling is currently achieved to satisfaction using a single or dual rubber septum to ensure a minimum of dirt is transferred to any samples. One common method is to use a system where a needle is encased in one septum, and when pushed against a second septum, the needle pierces both, creating a fluid pathway with very low risk of contamination. However, when the two surfaces of the two septa touch, infectious particles can be trapped between them and be transferred to the needle as it pierces and slides through the join between the two septa. In many processes where a nutrient medium is incubated, a single infectious particle may destroy the product.

According to the present invention there is provided an aseptic sampling system comprising: a sampler assembly and an interface assembly, each assembly comprising a housing, each housing defining a separate sterile enclosure for each of the assemblies; an air lock arranged to provide, in use, the aseptic joining of the sterile enclosures within the sampler and interface assemblies; and a re-sealable liquid connection mechanism positioned to operate within the air lock, wherein: the sampler assembly and interface assembly are arranged such that, when connected together, they form an outer protective surface comprising the housings of each of the sampler and interface assemblies, the outer protective surface providing a sterile internal enclosure and air lock and an air-tight barrier between the outer non-sterile atmosphere and the inner sterile atmosphere, and wherein the re-sealable liquid connection mechanism is contained within the sterile enclosure and contains at least one liquid connector from each of the sampler and interface assemblies and is configured such that, in use, at least one of the liquid connectors can move across the sterile enclosure and air lock to connect with the other connector in the liquid connection mechanism, without contacting any internal surfaces within the air lock.

The system may be arranged such that the liquid connectors, in use, can subsequently be re-sealed, disconnected and separated.

This invention provides a means of sampling where both the reservoir and sample remain free of contaminants that may be present in the atmosphere or on the surfaces of the sampling device and reservoir, and where many samples can be taken using the same equipment. Furthermore, the invention does not require external means of sterilization, for example, to inject high pressure steam or ethylene oxide. Rather the invention can be made from entirely disposable parts.

Examples of the present invention will now be described with reference to the accompanying drawings, in which:

FIGS. 1a and 1b are schematic diagrams showing the principle of the invention;

FIG. 5 shows a cut-away detail of the first preferred embodiment of the invention.

Figure 2:
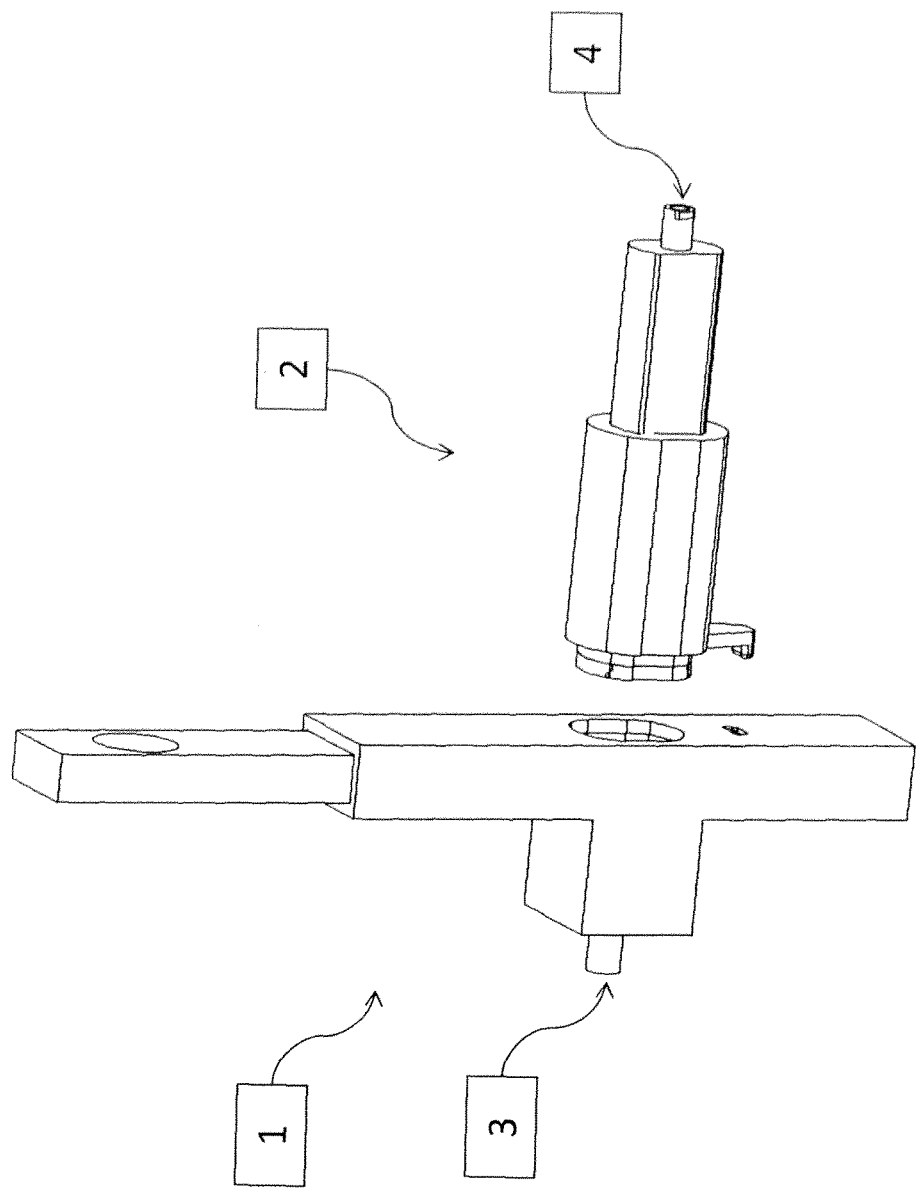
FIG. 2 shows the outward form of the first preferred embodiment of the invention.

The invention is an aseptic sampling system which comprises two mating assemblies shown schematically in FIG. 1a. A sampler assembly 2 whose function is to withdraw or infuse a single sample, and an interface assembly 1 whose function is to provide the interface between the sampler assembly and the reservoir 38 to be sampled. The interface assembly 1 is usually retained with the reservoir 38 for the duration of an aseptic culture, and allows the repeated taking of samples through the use of one or more units of the sampler assembly 2.

The sampler and interface assemblies 2,1 together comprise the following parts. Firstly, an outer protective surface is provided, made up of a housing 8,5 of each of the sampler and interface assemblies 11,6. This outer protective surface makes a sterile enclosure by forming a barrier between the outer non-sterile atmosphere and the inner sterile atmosphere. Secondly, an air lock is provided that allows the joining of the sterile enclosure in the sampler and interface assemblies. Thirdly, a re-sealable liquid connection mechanism is provided that contains a connector in each of the sampler and interface assemblies 2,1. At least one of the connectors is moved through the sterile enclosure and air lock to mate with the opposite connector in the liquid connection mechanism, without sliding on any surfaces that could be non-sterile.

The liquid connection mechanism, sterile enclosure 18, outer protective surface 5,8 and air lock 11,6 each are shown schematically and operated as shown in FIG. 1 and described as follows. First the sampler assembly 2 is mated with the interface assembly 1 via the air lock 11,6 (FIG. 1bi). The air lock is opened, keeping the sterile enclosure 18 free of contamination of outside air. Second, the parts of the liquid connection mechanism 7,9,10 are joined within the sterile enclosure, and without sliding past surfaces 11,6 of the air lock that may be non-sterile (FIG. 1bii). The liquid connection mechanism 7,9,10 thus creates a sealed aseptic liquid flow path. A sample is then infused or withdrawn from the reservoir 38. The sampler and interface assemblies 2,1 are then separated by reversing the above procedure: first the liquid connection mechanism 7,9,10 is resealed and separated, and then the air lock is disengaged.

The invention does not depend on particular forms of the component mechanisms. The novelty of this aseptic sampling system is the combination of a re-sealable liquid connection mechanism within a sterile enclosure 18, protected by an air lock 11,6 and an outer protective surface 5,8, so that the liquid connection can be made without the parts of the connection mechanism being exposed to outside air or being made to contact any surfaces that could be non-sterile, and that the liquid connection can be disconnected without contamination of the sampler or interface assemblies. These properties of the invention are necessary for the utility of the system: to take repeated samples without contamination of sample or reservoir 38, or the use of external sterilizing equipment.

The description below starts with to a first embodiment, but the invention is not limited to the geometry, mechanisms and motions described below.

The first embodiment, as shown in FIG. 2, comprises two mechanical assemblies, an interface assembly 1 and a sampler assembly 2. The interface assembly provides a connector 3 to a reservoir and the sampler assembly provides a connector 4 to a sample vessel. FIG. 2 shows female luer connectors for features 3 and 4. However, alternative embodiments would include barbed tube fittings, flanged sanitary fittings and flanged welded seals to connect to disposable bag bioreactors or disposable sampling bags.

Each mechanical assembly comprises separate parts, detailed in the cross section diagram of FIG. 3. The interface 1 comprises a housing 5, shutter 6, and liquid valve 7. The connector to the reservoir is here a moulded pipe fitting 3 on the outside of the housing 5. The sampler 2 comprises a housing sheath 8, slider 9, inner cap 10 and outer cap 11. The shutter 6 is locked in position in the housing 5 by an interlock hook 15, which fits in an interlock aperture 16.

Figure 3A:
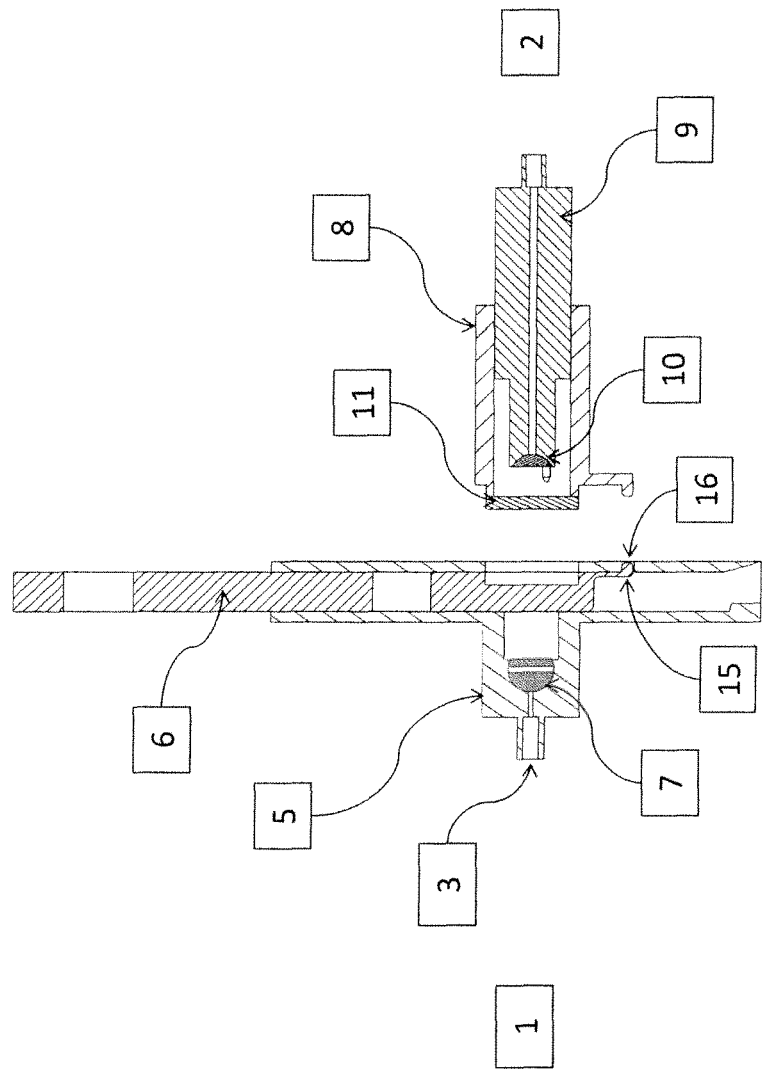
FIGS. 3a to 3e show the mechanism and operation of the first preferred embodiment of the invention.

The operating mechanism and sequence for the first embodiment is described with reference to FIGS. 3a-3e. FIG. 3a shows the first embodiment before sampling.

Figure 3B:
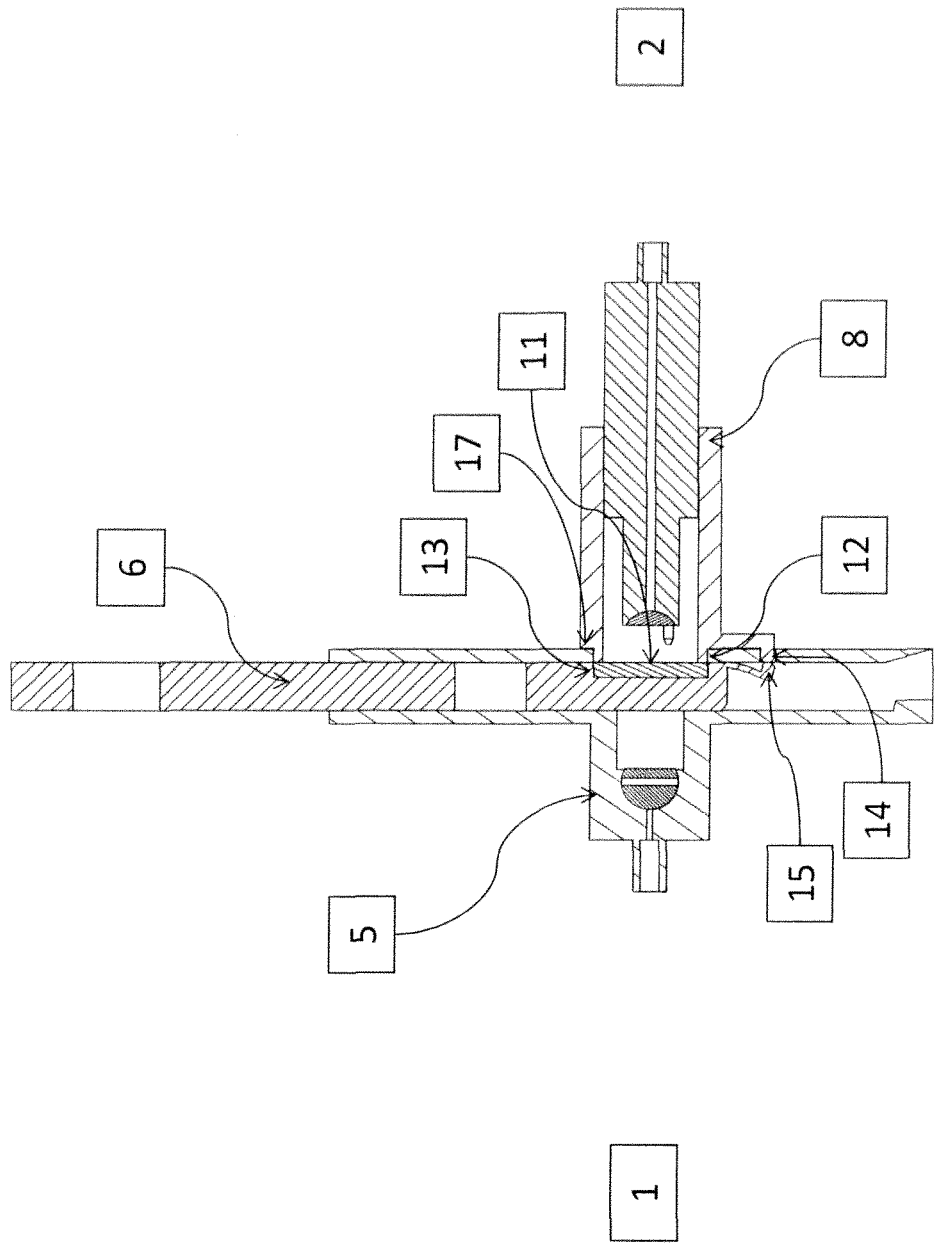

The first step of sampling is shown in FIG. 3b, where the sampler assembly 2 is pushed into a mating aperture 12 of the interface assembly 1. The outer cap 11 is then fully contained in a slot 13 of the shutter 6. Simultaneously an interlock protrusion 14 pushes the interlock hook 15 out of the interlock aperture 16. This allows the shutter 6 to slide vertically. The mating faces of the housing sheath 8 and housing 5 form an air-tight surface 17.

Figure 3C:
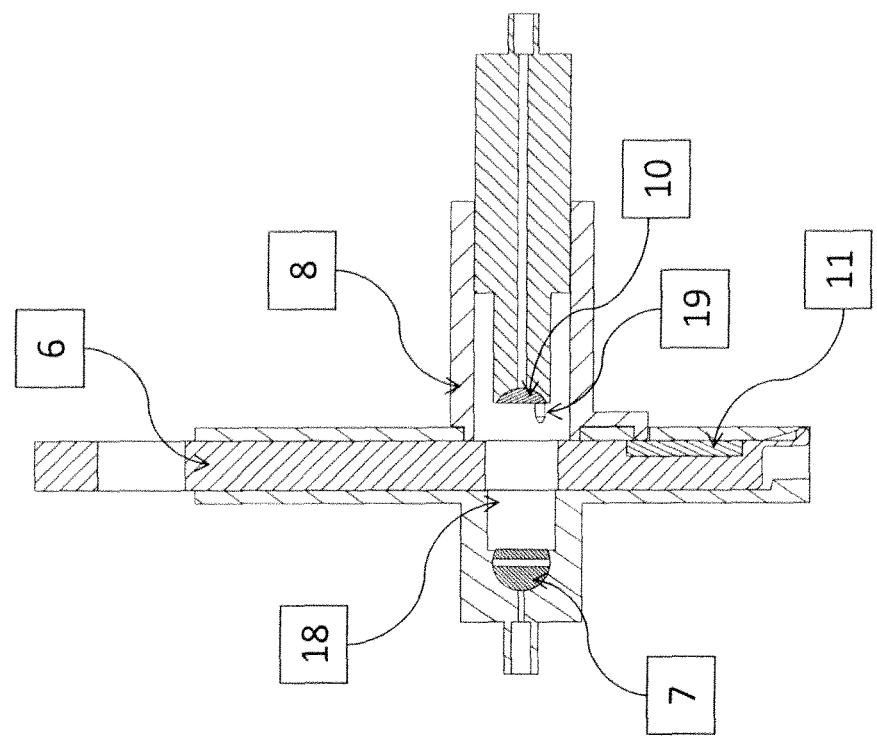

The second step of sampling is shown in FIG. 3c, where the shutter 6 is slid down. This moves the outer cap 11 away from the housing sheath 8 which has the effect of joining the sterile atmospheres in the sampler and interface assemblies 2,1 into a single sterile enclosure 18. At this point, the sterile enclosure 18 contains a direct path between the inner cap 10 and the liquid valve 7, while the outer cap 11 is fully stored away from the sterile enclosure 18.

Figure 3D:
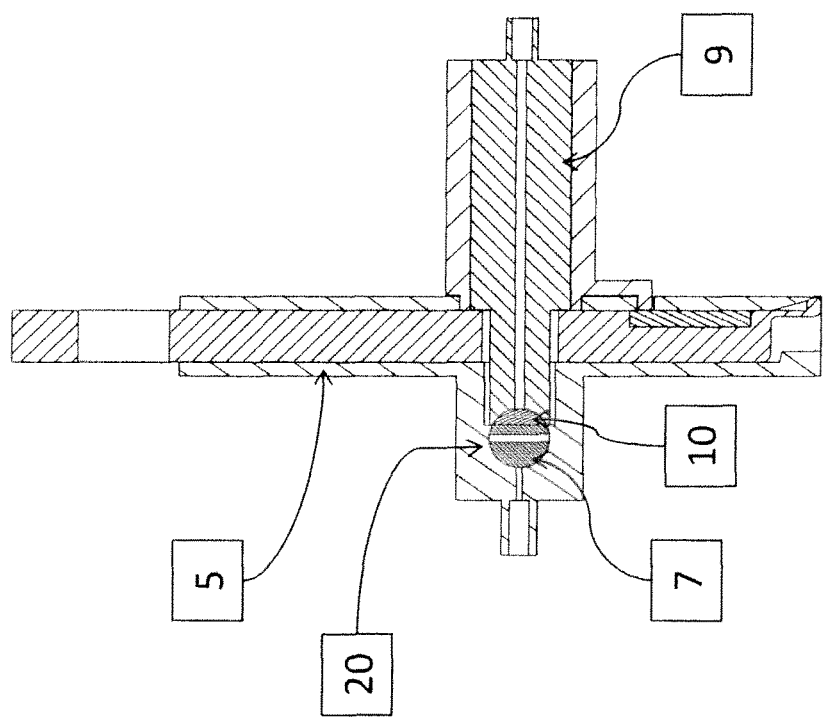

The third step of sampling is shown in FIG. 3d. The slider 9 is now pushed towards the interface assembly so that the inner cap 10 mates with the liquid valve 7. The inner cap 10 contains a registration feature 19 that mates with an indentation on the liquid valve 7. The liquid valve 7 and the inner cap 10 form a continuous, sealing, cylindrical sliding surface 20 within the housing 5.

Figure 3E:
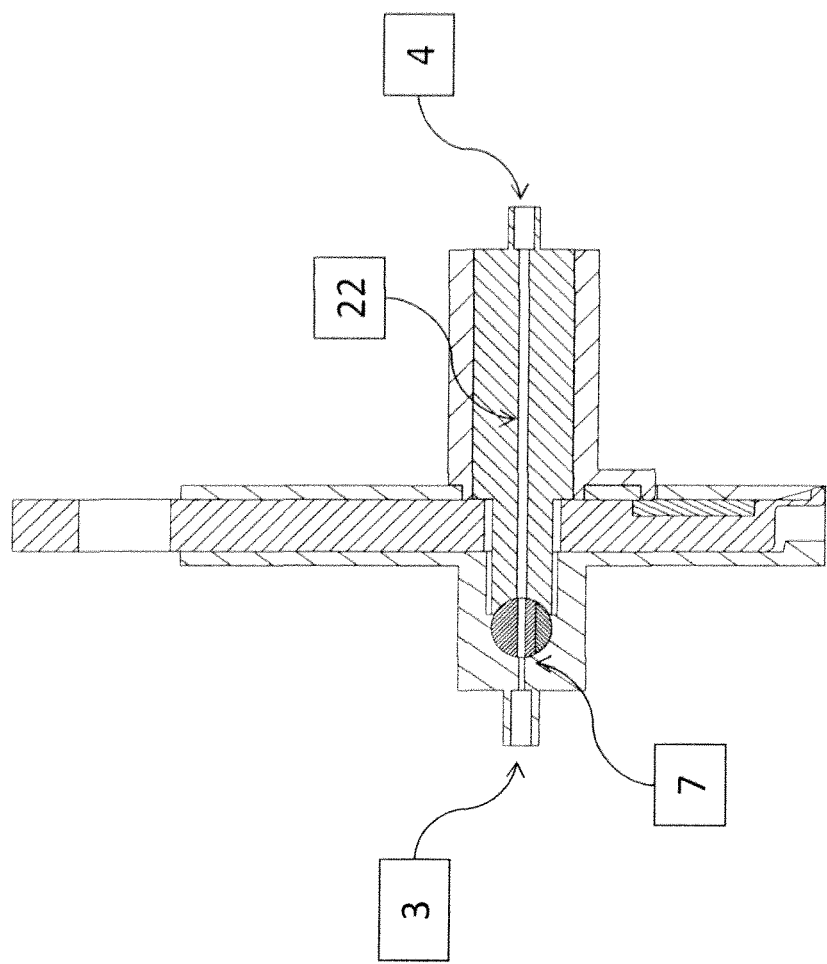

The fourth step of sampling is shown in FIG. 3e. The liquid valve 7 is rotated to the open position, such that the channel 22 now forms an open path between connector 3 from the reservoir and connector 4 to the sample vessel. The sample then flows through using the positive pressure of the reservoir or by applying suction to the sample vessel.

Having taken the sample, the sampler assembly 2 is then removed. The movements are exactly opposite to the four steps above, leading to the disconnection of the sampler assembly 2 as shown in FIG. 3a.

Additional details of the first embodiment are as follows.

Figure 6:
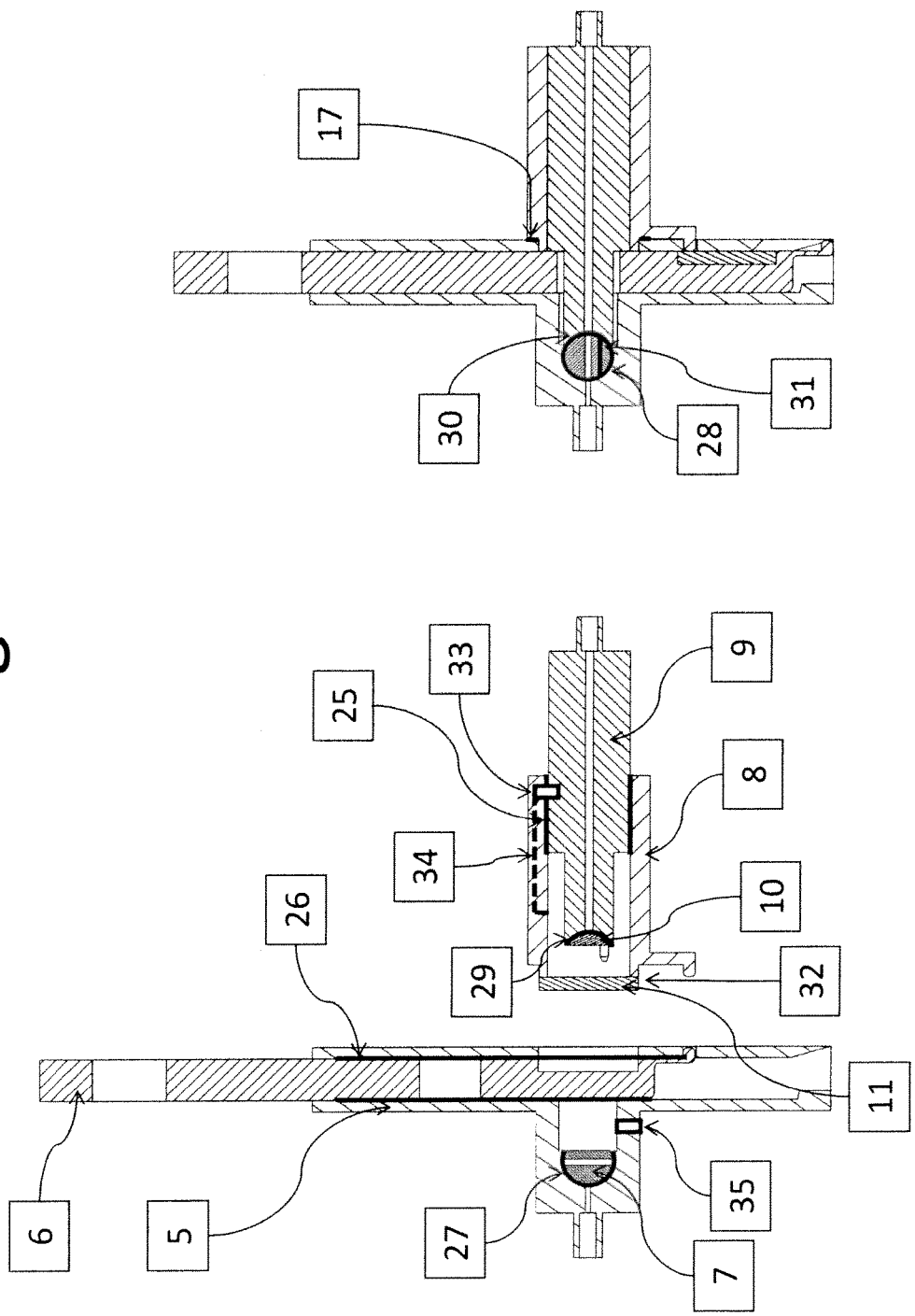
FIG. 6 shows further descriptions of the first preferred embodiment of the invention.

As shown in the cross-section illustration in FIG. 5, tab features 23 may be provided on the housing sheath 8 to interlock with slots 24 in the shutter 6 so that the housing sheath 8 is held against the housing 5 in order to create an air seal between the two parts. FIG. 6 shows the location of this air seal 17, which also includes a compliant material on at least one of the two mating surfaces. Similar tab features can be provided between components shown in FIG. 3a: between the outer cap 11 and the housing sheath 8 and between the inner cap 10 and the slider 9.

The sealing surfaces that are required for the preferred embodiment are shown in FIG. 6, and are: the surface 17 between the housing sheath 8 and the housing 5; the surface 25 between the housing sheath 8 and the slider 9; the surface 26 between the housing 5 and the shutter 6; the surface 27 between the housing 5 and the liquid valve 7; the surface 28 between the housing 5 and the inner cap 10; the surface 29 between the slider 9 and the inner cap 10; the surface 30 between the slider 9 and the liquid valve 7; the surface 31 between the inner cap 10 and the liquid valve 7; and the surface 32 between the housing sheath 8 and the outer cap 11.

All sealing surfaces can be made by incorporation of a compliant material on at least one surface in each pair of the parts listed above or by incorporation of an additional, compliant sealing component such as an O-ring between the mating surfaces of pairs of parts.

A further optional feature which limits the range of movement between the slider 9 and the housing sheath 8 is shown in FIG. 6. Here a post 33 is attached to the slider 9 and runs within a groove 34 in the housing sheath 8. The post 33 ensures that the slider 9 cannot be pulled completely out of the housing sheath 8.

A gas permeable vent 35 which is assembled into the housing 5 is also shown in FIG. 6. This vent 35 ensures that displacement of air caused by motion of internal parts does not generate an air pressure change within the sterile enclosure 18 described in FIG. 3c. The vent 35 also ensures that changes in external air pressure do not generate a leakage of air between any of the sealing surfaces described previously. The vent is likely to be made of a filter material that excludes particles of greater that 0.22 µm in diameter.

A variation on this embodiment is to use a different liquid connection mechanism such that the liquid valve 7 and inner cap 10 are replaced with alternative linear or rotary valve mechanisms. Such valves are well known in the art.

A further variation of this embodiment is a modification of the shutter 6 and housing 5, so that the shutter describes a circular sliding motion rather than a linear sliding motion.

A second embodiment of the invention is shown in FIGS. 4a-4e. This embodiment is consistent with the principle of the invention and the sequence of steps is similar to the first embodiment. The differences from the first embodiment are described below.

Figure 4A:
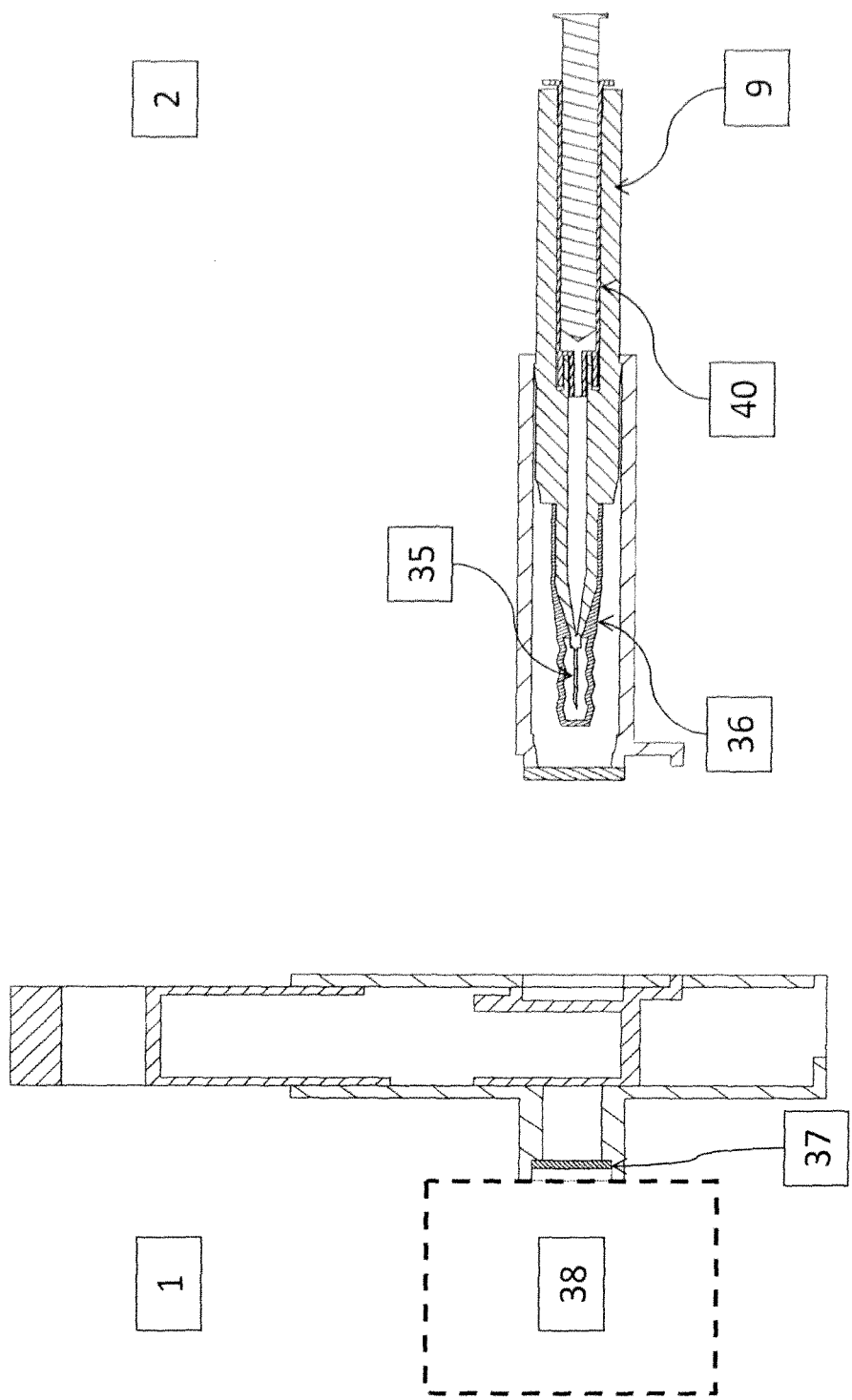
FIGS. 4a to 4e show the mechanism and operation of the second preferred embodiment of the invention.
Figure 4B:
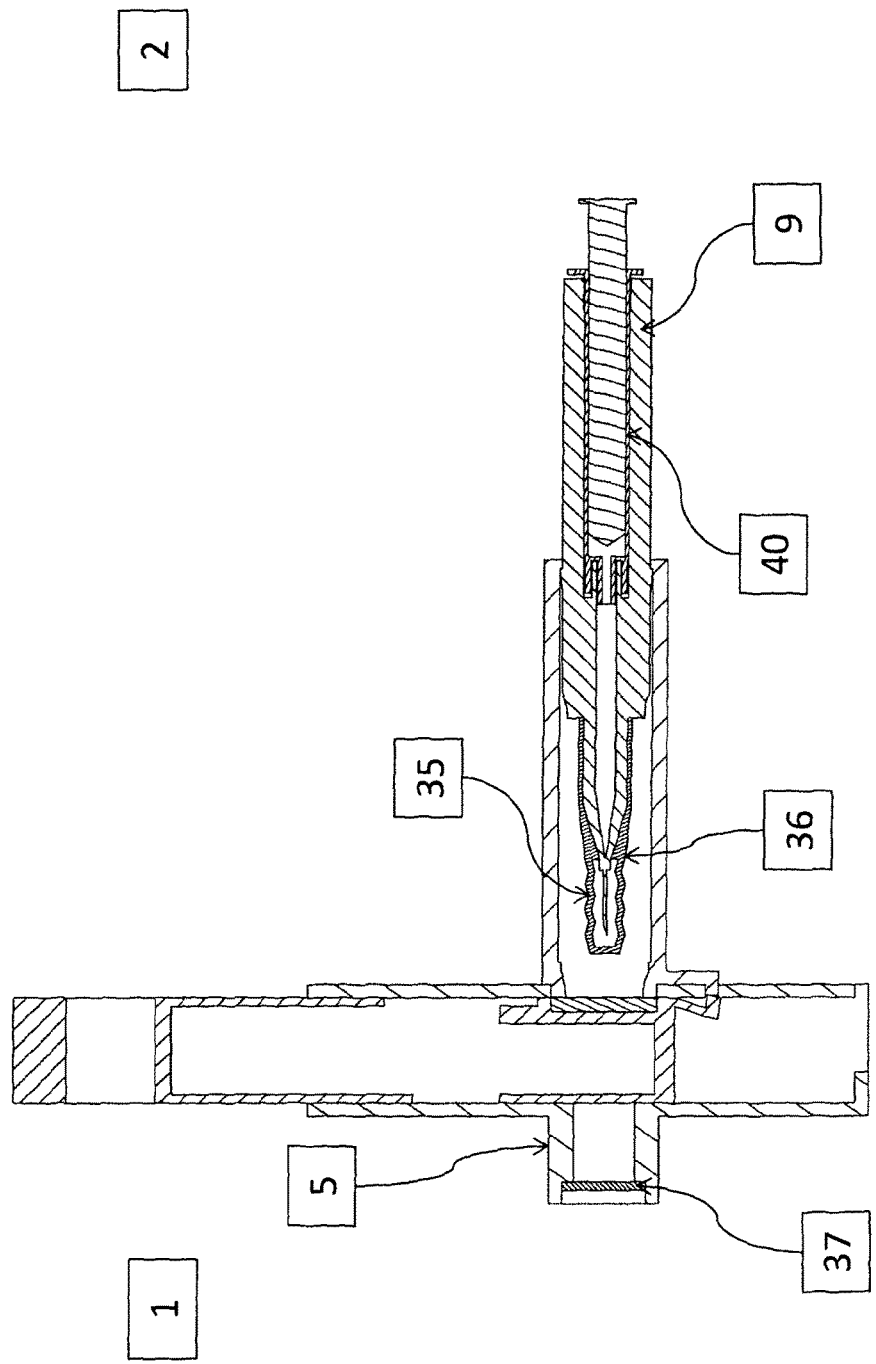
Figure 4C:
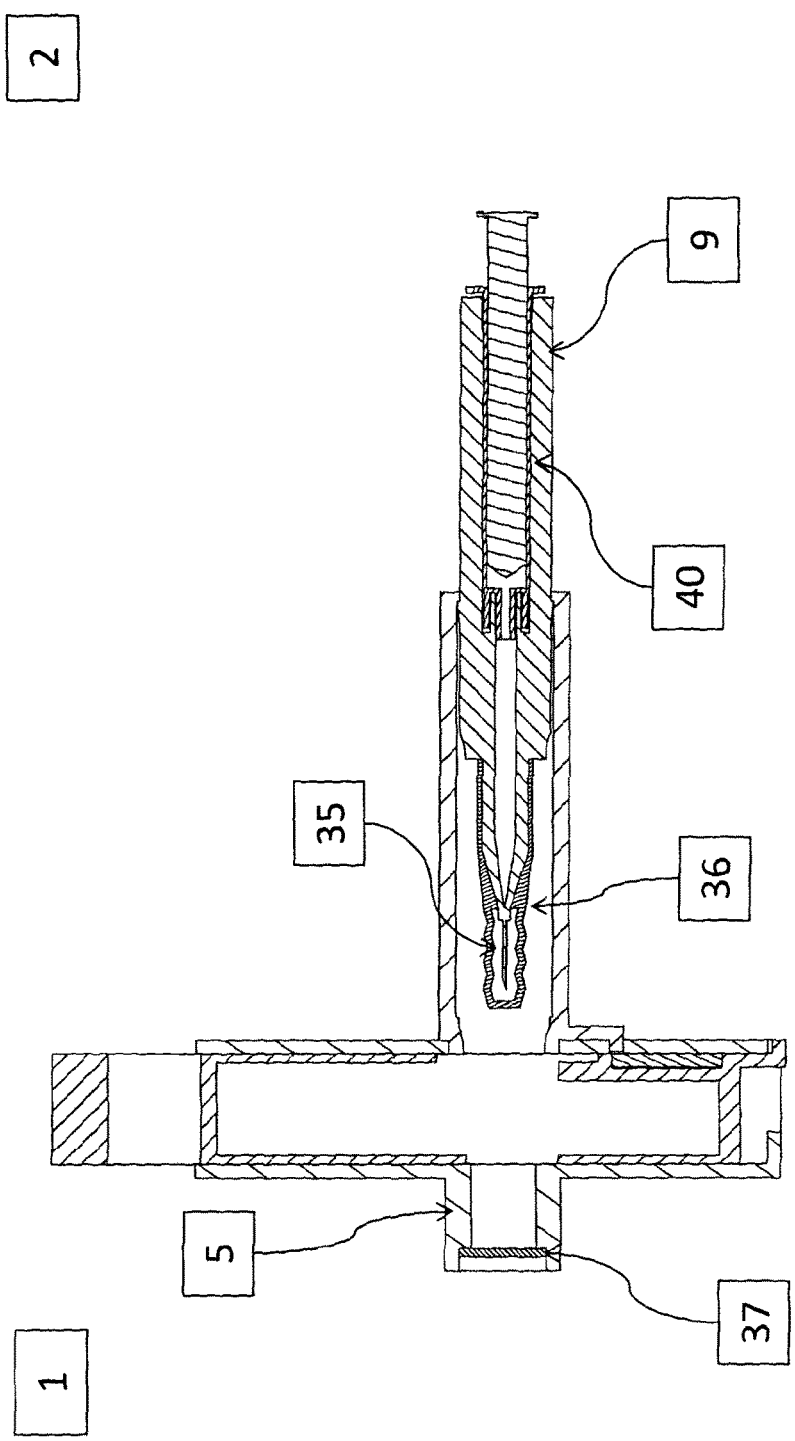
Figure 4D:
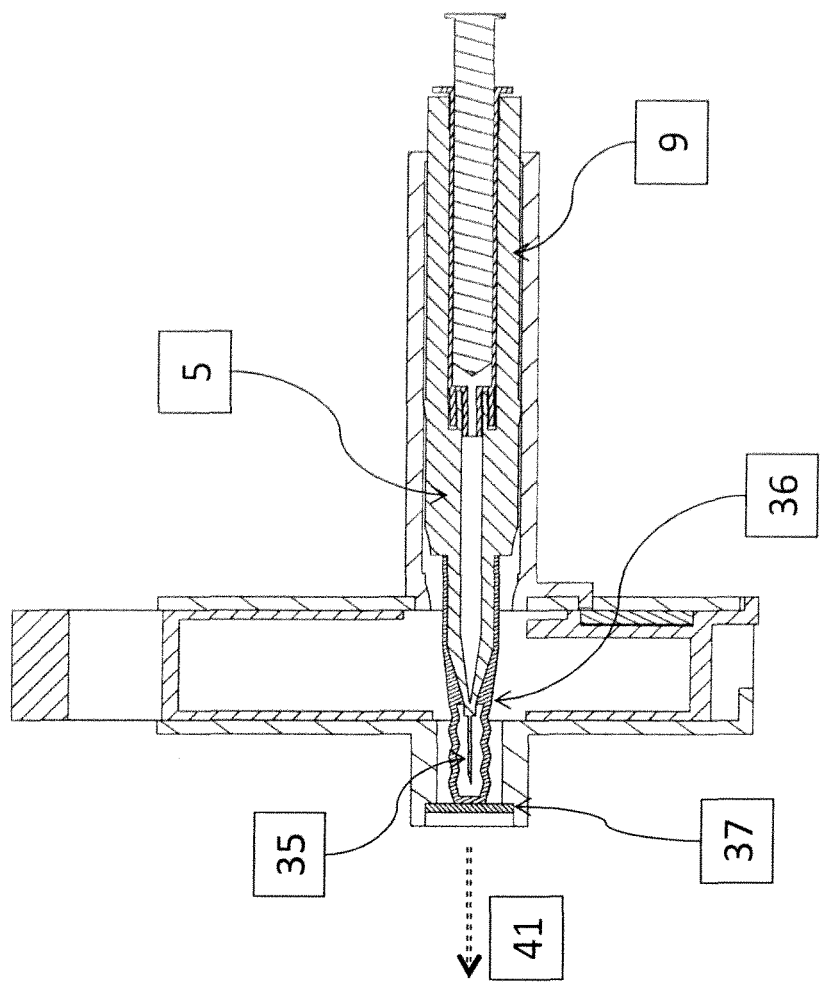
Figure 4E:
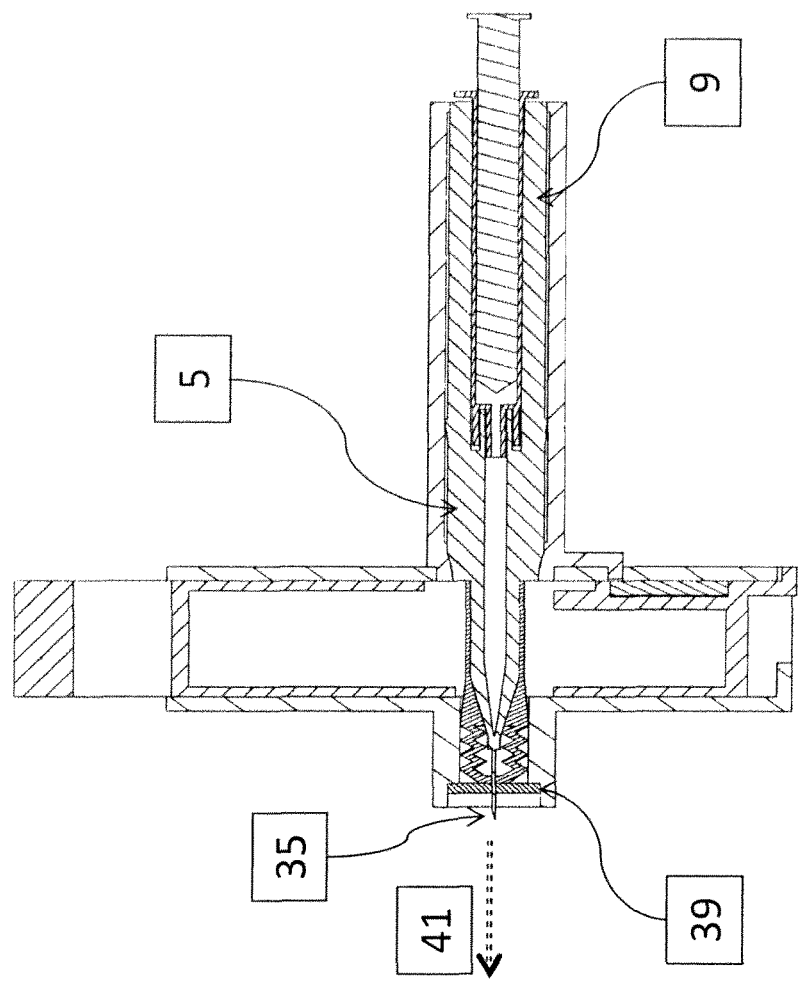

As shown in FIG. 4a, the liquid connection mechanism in this case comprises a needle 35 and a pair of septa: a sample septum 36 and an interface septum 37. The interface septum 37 seals the interface assembly 1 from the reservoir 38. FIGS. 4b to e show the sequence of operations to connect the sampler assembly 2 to the contents of the reservoir 38. Referring to FIGS. 4b-4e, the difference from the operational sequence of the first embodiment (FIGS. 3b-3e) is that the liquid connection is now made by pushing the slider 9 directly through the position shown in FIG. 4d to the position shown in FIG. 4e as shown by the arrow 41. Thus the needle 35 pierces both septa 36 and 37 and enters the reservoir 38 so that an aseptic liquid connection 39 is made. Removal of the sampler is performed by reversing the sequence of steps in FIGS. 4b to 4e. The septa 36 and 37 are both made of an elastomeric material that has the ability to reseal the pierced hole after removal of the needle. The interface septum 37 is designed to ensure that when the needle 35 is removed, the interface septum 37 can still maintain both a liquid and air tight seal, even after multiple piercings. One possible embodiment of the sampling vessel is a syringe 40 as shown in FIG. 4a.

The invention claimed is:

1. An aseptic sampling system comprising: a sampler assembly and an interface assembly, each assembly comprising a housing, each housing defining a separate sterile enclosure for each of the assemblies; an air lock arranged between the sampler assembly and the interface assembly, to connect the sampler assembly and the interface assembly and provide aseptic joining of the sterile enclosures within the sampler and interface assemblies, the aseptic joining forming a sterile internal enclosure; and a re-sealable liquid connection mechanism positioned to operate within the aseptic joining of the sterile enclosures, the liquid connection mechanism comprising a rotating valve comprising two parts that, when joined, form a sealing cylindrical sliding surface and at least one internal channel that, when the two parts are rotated, forms an open path, wherein: the sampler assembly and the interface assembly are arranged such that, when connected together by the sampler assembly inserted in the interface assembly, the sampler assembly and the interface assembly form an outer protective surface comprising the housings of each of the sampler and the interface assemblies, providing the sterile internal enclosure and an air-tight barrier between an outer non-sterile atmosphere and an inner sterile atmosphere, and wherein the re-sealable liquid connection mechanism is contained within the sterile enclosures and contains at least one liquid connector from each of the sampler and the interface assemblies and is configured such that, in use, at least one of the liquid connectors can move across the internal sterile enclosure and air lock to connect with the other liquid connector, without contacting any internal surfaces within the air lock, where the air lock comprises an outer cap in the sampling assembly which mates with a shutter that slides within the interface assembly housing.

2. An aseptic sampling system according to claim 1, where the shutter slides in a linear path.

3. An aseptic sampling system according to claim 1, where the shutter slides in a path of a circle or an arc.

4. An aseptic sampling system according to claim 1, configured such that the liquid connectors, in use, can subsequently be re-sealed, disconnected and separated.

5. A method of aseptic sampling comprising:
aseptically joining the sterile enclosures within the sampler and the interface assemblies of the aseptic sampling system of claim 1;
moving at least one of the liquid connectors move across the sterile enclosure and air lock and connecting with the other connector in the liquid connection mechanism, without contacting any internal surfaces within the air lock, including mating the outer cap of the air lock in the sampling assembly with the shutter, sliding the shutter within the interface assembly housing, and rotating the two parts of the rotating valve to form an open path; and;
infusing or withdrawing a sample from a reservoir and through the interface and the sample assemblies.

6. The method of claim 5, comprising sliding the shutter in a linear path.

7. The method of claim 5, comprising sliding the shutter in a path of a circle or an arc.

8. The aseptic sampling system of claim 1, wherein the sampling assembly further comprises an interlock protrusion, and the interface assembly further comprising an interlock hook and an interlock aperture, the interlock hook fitting in the interlock aperture, and wherein the shutter is locked in position by the interlock hook in the interlock aperture until the interlock protrusion of the sampling assembly pushes the interlock hook out of the interlock aperture and allows the shutter to slide.

* * * * *